(12) United States Patent
Melling et al.

(10) Patent No.: US 6,310,348 B1
(45) Date of Patent: Oct. 30, 2001

(54) SPECTROSCOPIC ACCESSORY FOR EXAMINING FILMS AND COATINGS ON SOLID SURFACES

(75) Inventors: Peter J. Melling, Sturbridge, MA (US); Paul H. Shelley, Lakewood, WA (US)

(73) Assignee: Ramspec Corporation

( * ) Notice: Subject to any disclaimer, the term of this patent is extended or adjusted under 35 U.S.C. 154(b) by 0 days.

(21) Appl. No.: 09/344,692

(22) Filed: Jun. 25, 1999

(51) Int. Cl.[7] .................................................. G01N 21/01
(52) U.S. Cl. ...................... 250/341; 250/339.11; 356/244
(58) Field of Search .................... 250/339.11, 339.08, 250/339.07, 340, 341.1, 341.2, 341.4, 341.8, 347, 353; 356/445, 446, 244

(56) References Cited

U.S. PATENT DOCUMENTS

| | | | | |
|---|---|---|---|---|
| 5,019,715 | * | 5/1991 | Sting et al. ........................ | 250/559.1 |
| 5,048,970 | * | 9/1991 | Milosevic et al. .................... | 356/445 |
| 5,075,551 | * | 12/1991 | Watanabe ............................ | 250/341.3 |
| 5,160,826 | * | 11/1992 | Cohen et al. .................... | 250/339.08 |
| 5,170,056 | * | 12/1992 | Berard et al. ...................... | 250/341.4 |
| 5,184,191 | * | 2/1993 | Krishnan ................................. | 356/244 |
| 5,406,082 | * | 4/1995 | Pearson et al. ................. | 250/339.01 |
| 5,793,042 | * | 8/1998 | Quick .............................. | 250/339.08 |
| 5,895,918 | * | 4/1999 | Powell et al. .................... | 250/339.11 |
| 5,910,842 | * | 6/1999 | Piwonka-Corle et al. ........... | 356/359 |
| 5,995,289 | * | 11/1999 | Hwu et al. ............................ | 359/627 |

\* cited by examiner

Primary Examiner—Constantine Hannaher
Assistant Examiner—Albert Gagliardi (57) ABSTRACT

An accessory for an FTIR spectrometer comprises fiber-optic cables connected to a framework within which two mirrors are housed. The mirrors, which are preferably off-axis parabolas, are positionable with respect to each other and with respect to the ends of the fiber-optic cables. The beam from the first cable is reflected by the first mirror onto a sample surface at or near the grazing angle, after which it is captured by the second mirror and focused onto the end of the return cable which transmits it back to the spectrometer. Very thin films and coatings can be spectroscopically detected and characterized using the accessory.

12 Claims, 7 Drawing Sheets

SPECTROSCOPIC ACCESSORY FOR EXAMINING FILMS AND COATINGS ON SOLID SURFACES

BACKGROUND OF THE INVENTION

This invention relates to reflectance spectroscopy of surfaces which are fully or partially covered with films, coatings, or contamination, and in particular to an accessory for use therein.

Fourier transform infrared (FTIR) spectroscopy is a powerful and widely used analytical technique. When it is applied to solid surfaces, three different techniques of reflectance spectroscopy can be used: specular reflectance, diffuse reflectance, and reflection-absorption spectroscopy (see P. R. Griffiths and J. A. de Haseth, *Fourier Transform Infrared Spectroscopy*, Wiley-Interscience, 1986, chapter 5.III). Specular reflectance is used on flat, clean surfaces and spectra are readily obtained from comparatively small samples at incidence angles of about 15–75°. Diffuse reflectance spectra are commonly obtained from matte or rough surfaces, or from the surface of powdered samples, often using specially designed spectrometers or accessories. The third type of reflectance spectrum, commonly called a reflection-absorption spectrum, is fairly easily obtained from surfaces coated with thick films in the range of 0.2–20 $\mu$m. Simple reflectance spectra obtained from such surfaces are in effect transmission spectra obtained while the spectrometer radiation passes through the film before and after being reflected from the surface. However, in the case of extremely thin layers, such as monomolecular layers, the path length through the film may be too short to afford a usable spectrum. In practice, layers less than about 10 $\mu$m thick cannot be successfully detected or characterized using conventional specular or diffuse reflectance geometries. This problem has been recognized, and the method commonly known as "grazing angle" FTIR has been developed. The method is explained in detail by Griffiths and de Haseth (op. cit., p. 189). Briefly, the thickness d (in $\mu$m) of a film which will give a reflectance-absorption spectrum of the same intensity as the transmittance spectrum of a 10 $\mu$m film is given by the expression:

$$2d = 10 \cos\alpha$$

where $\alpha$ is the angle of incidence (measured from the perpendicular). As $\alpha$ approaches the grazing angle, the effective path length of the radiation through the film is increased. It is therefore advantageous to arrange for the radiation to strike the surface under examination at an angle approaching the grazing angle. Spectrometer accessories which allow for variable angles of approach by the radiation, such as those proposed by Milosevic and Harrick (U.S. Pat. No. 5,048,970) are available for this purpose.

It is a disadvantage of these prior-art accessories that they are placed inside the sample compartment of the spectrometer, so that samples have to be brought to the spectrometer, and must be of limited size. Methods are known for utilizing optical fiber cables to enable in-situ spectroscopic sampling of a wide range of different types of samples (see, for example, U.S. Pat. Nos. 5,170,056 by Berard, Burger, Melling and Moser and U.S. Pat. No. 5,754,722 by Melling).

It is an object of the invention to combine the spectroscopic advantages of the grazing-angle method with the ease and convenience of using a fiber-optic cable to provide a spectroscopic means for characterizing and quantifying thin films on reflective surfaces such as metals, without the inconvenience and impracticality of removing samples to the spectrometer.

DETAILED DESCRIPTION OF THE INVENTION

Figure 1:
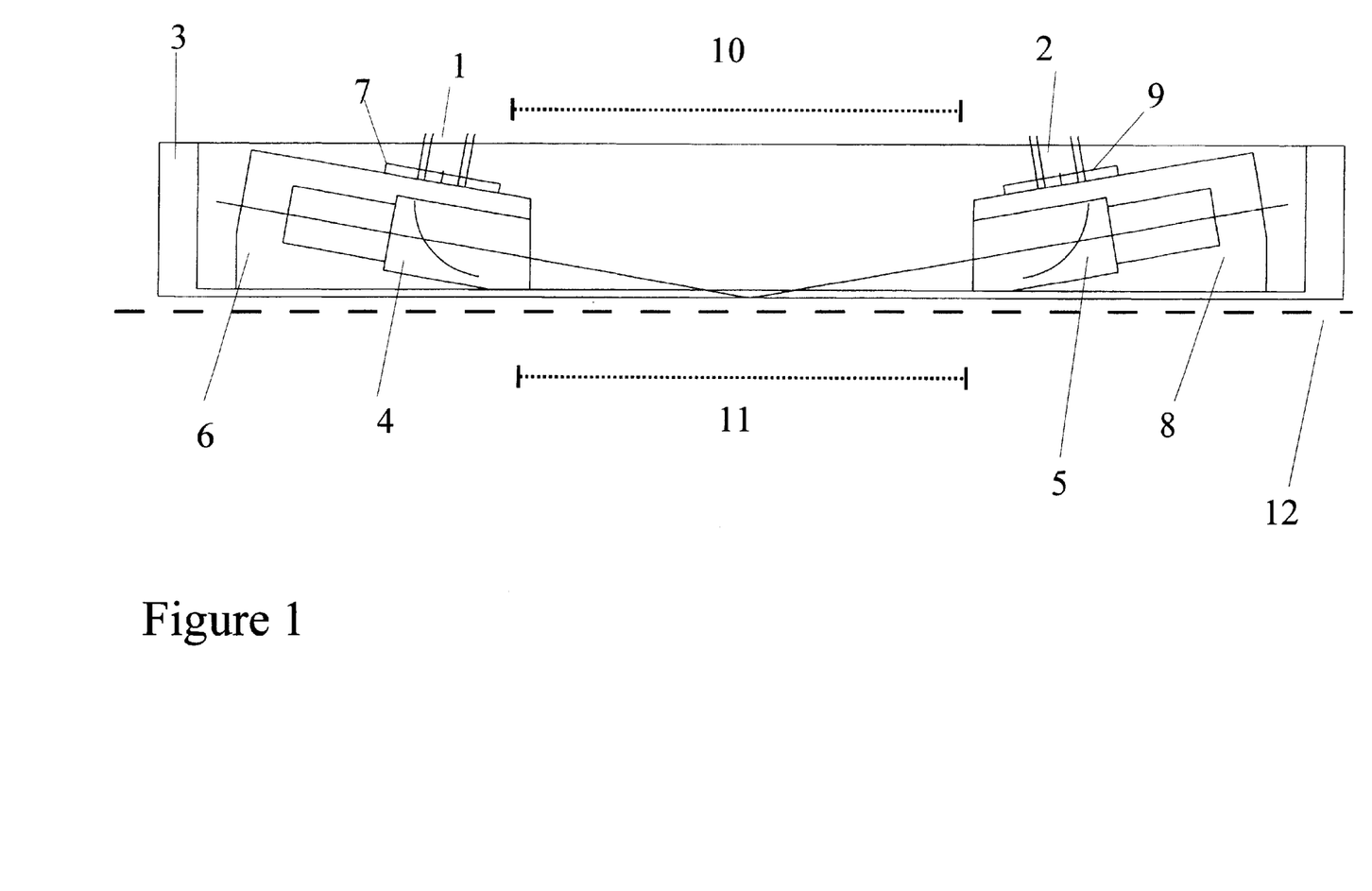
FIG. 1: Schematic cross-section of a grazing-angle accessory with 2 cables

A schematic drawing of one preferred embodiment of the invention is shown in FIG. 1. In this particular embodiment, a first fiber-optic cable (1) transmits radiation from a radiation source to the accessory, and a second fiber-optic cable (2) carries reflected radiation away from the accessory to a radiation detector. The $1^{st}$ fiber-optic cable (1) is attached to a $1^{st}$ positionable mirror support (6) by an attachment means (7) which is itself, independently, positionable. The $1^{st}$ positionable mirror (6) accommodates a mirror (4) and is itself accommodated within a supporting framework (3). In the most preferred embodiment, the positionable attachment means (7) allows for adjustment in three dimensions, so that the end of the fiber-optic cable (1) may be positioned at the focus of the $1^{st}$ mirror (6). The $1^{st}$ mirror is most preferably of the type known in the art as an off-axis parabola, so that the divergent radiation which is transmitted from the end of the $1^{st}$ fiber-optic cable is reflected from the mirror in the form of a collimated beam. Further, the $1^{st}$ mirror is most preferably positioned within the $1^{st}$ positionable mirror support (6) at such an angle that the said collimated beam of radiation is reflected by the mirror towards the surface under examination (12) at or near the above-described grazing angle, thus maximizing the distance traveled by the radiation through any film or coating which may be present on the said surface.

The $2^{nd}$ fiber-optic cable (2) is attached to a 2nd positionable mirror support (8) by an attachment means (9) which is itself, independently, positionable. The positionable mirror support (8) accommodates a $2^{nd}$ mirror (5) and is itself accommodated within the supporting framework (3). In the most preferred embodiment, the positionable attachment means (9) allows for adjustment in three dimensions, so that the end of the fiber-optic cable (2) may be positioned at the focus of the $2^{nd}$ mirror (5). In the most preferred embodiment, the said $2^{nd}$ mirror is of the off-axis parabola type, so that the collimated beam which is reflected from the surface will be focused onto the end of the $2^{nd}$ fiber-optic cable (2). Further, the 2nd mirror is most preferably positioned within the 2nd positionable mirror support (8) at such an angle that it may, in optimal fashion, collect radiation reflected from the surface (12) at or near the grazing angle. The said $2^{nd}$ mirror is most preferably positioned, using the positionable mirror support (8), such that a beam of radiation which has been transmitted from the $1^{st}$ fiber-optic cable (1), collimated by and reflected from the $1^{st}$ mirror (4) onto the surface (12), is reflected from the said surface onto the said $2^{nd}$ mirror (5), from which is reflected and focused onto the end of the $2^{nd}$ fiber-optic bundle.

Figure 2:
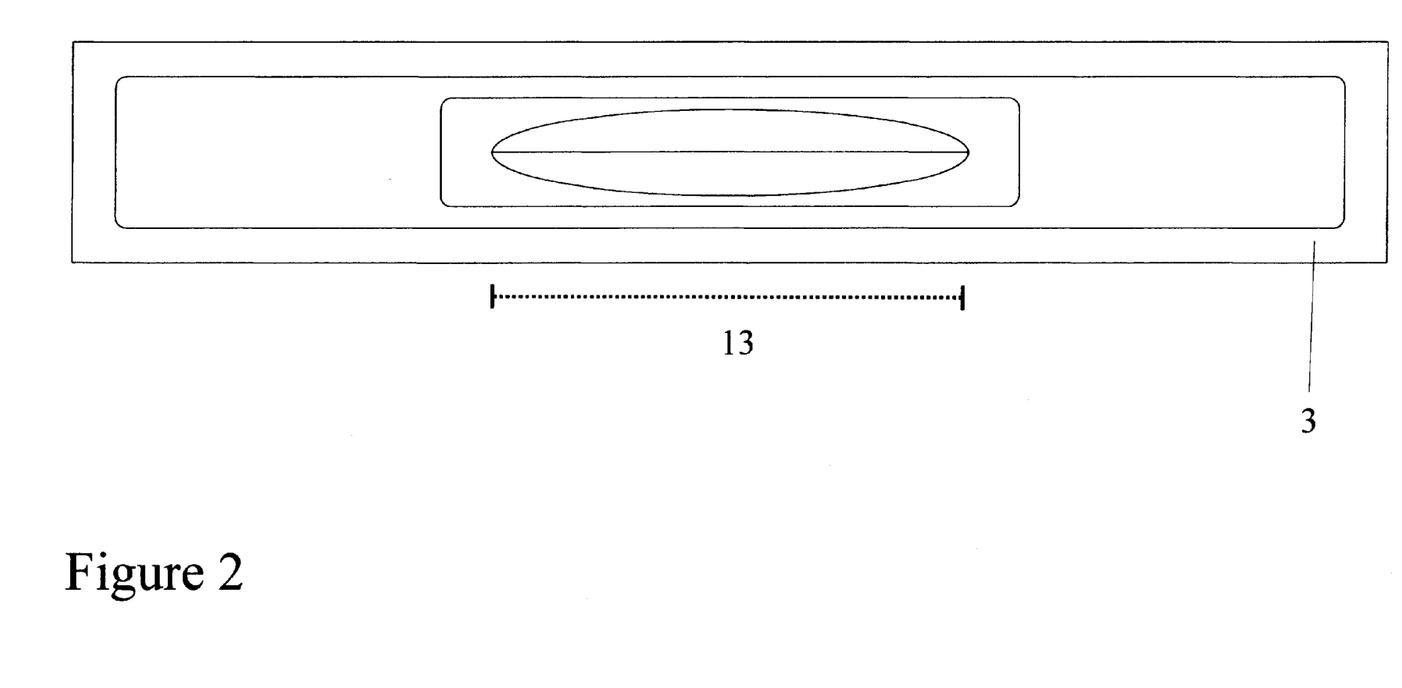
FIG. 2: Plan of the accessory showing the radiation spot size

By adjusting the relative position of the $1^{st}$ and $2^{nd}$ mirrors, it is possible to maximize the size of the radiation spot on the surface (13) while maintaining the radiation beam at or near the grazing angle as it approaches and leaves the surface.

Figure 3:
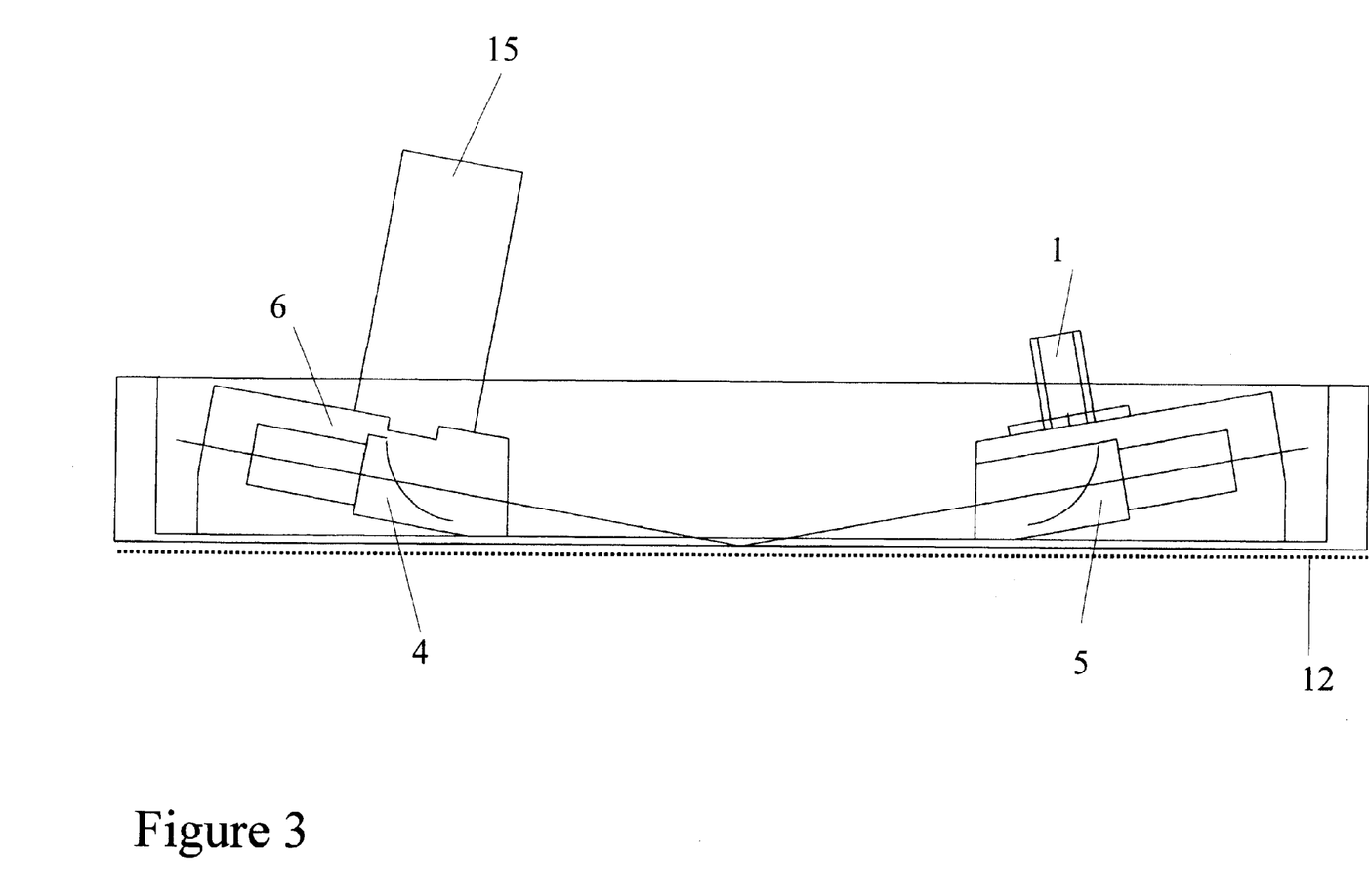
FIG. 3: Schematic cross-section of an accessory with a cable and a detector

A second preferred embodiment of the invention is shown schematically in FIG. 3. In this embodiment, a radiation detector is attached to the 2nd positionable mirror support (8). Radiation from the radiation source is transmitted through the fiber-optic cable (1) onto the mirror (5), where it is collimated and reflected onto the sample surface (12) at or near the grazing angle. From the sample surface, the radiation is reflected onto the mirror (4) which focuses it directly onto the radiation detector (150 which is attached to the mirror support (6). In a most preferred embodiment, the detector (15) is a mid-infrared detector such as a mercury-cadmium-telluride (MCT) detector or an DTGS detector, and the radiation source is a Fourier transform mid-IR spectrometer.

It will be apparent to those skilled in the art that the above discussion provides descriptions of only two possible embodiments of this invention and that other embodiments are possible. For example, an infra-red source can be used to supply radiation directly to the accessory, in combination with a, in combination with a fiber-optic cable which transmits the reflected signal back to an FTIR spectrometer. The invention will be further illustrated by describing examples of its use:

EXAMPLE 1

Figure 4A:
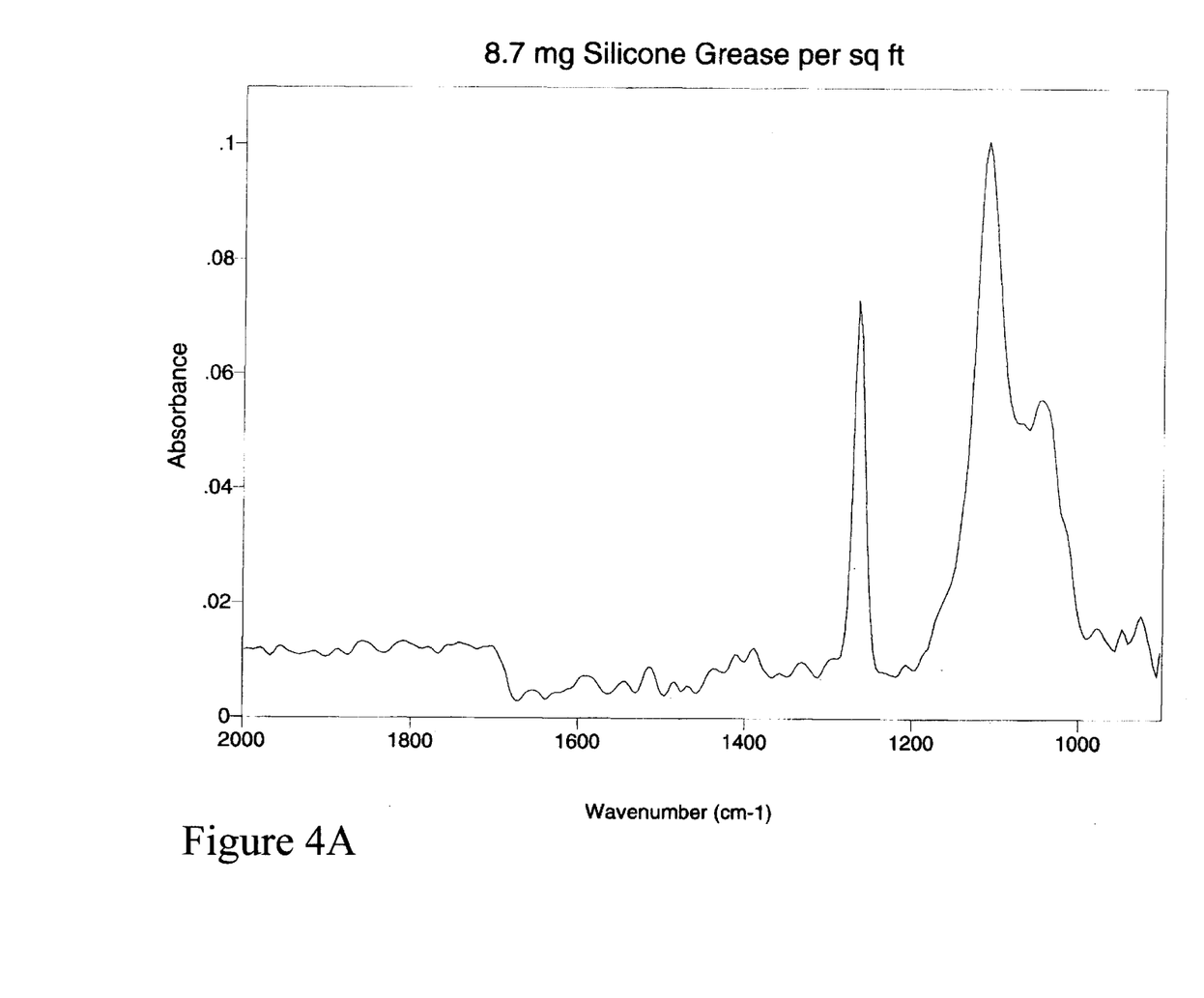
FIGS. 4A/4B: Grazing-angle FTIR spectra of silicone grease films on aluminum billets
Figure 4B:
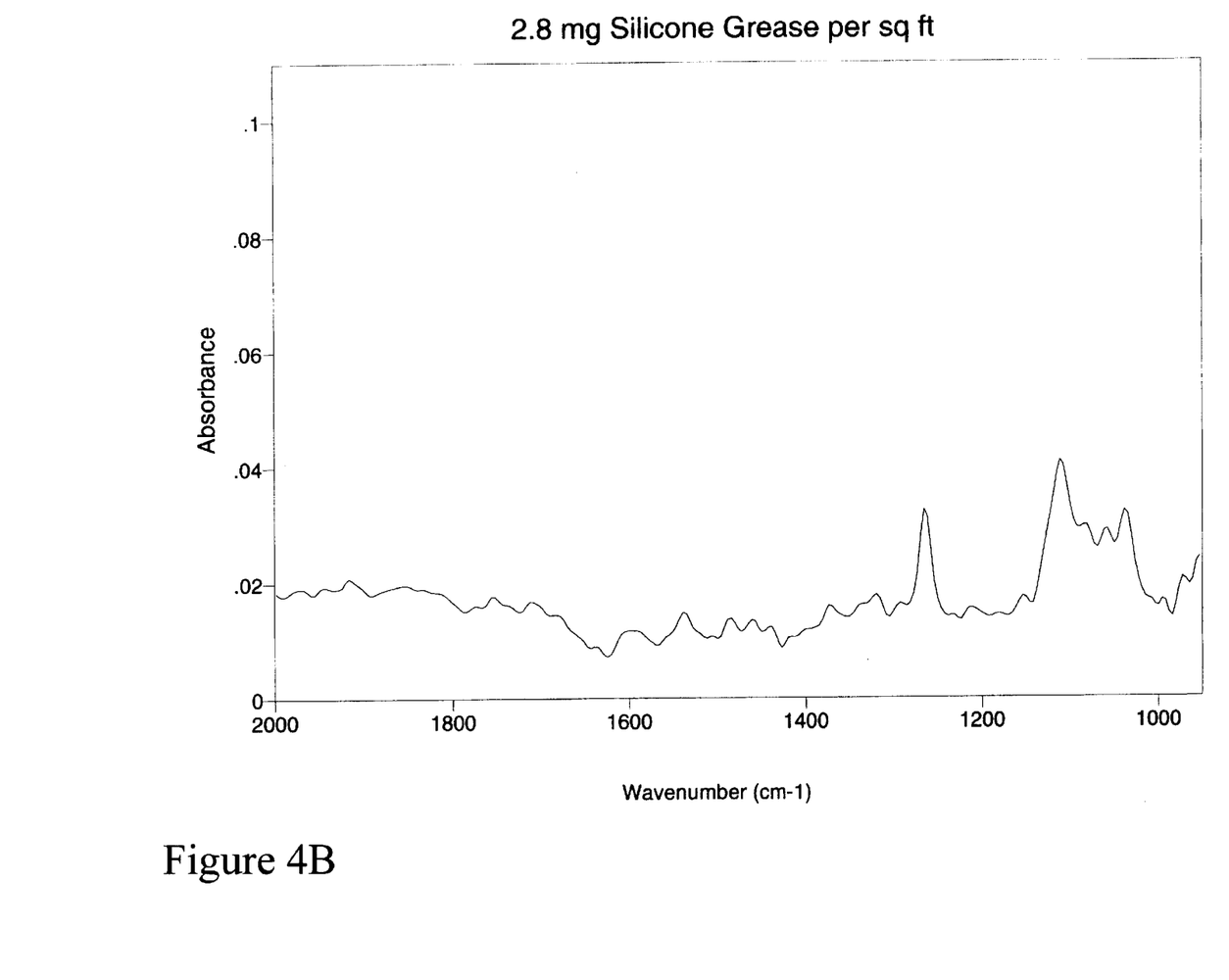

Two pieces of aluminum billet (each 6×6×0.1 inches in size) with smooth, shiny surfaces were weighed, then air-brushed with a silicone grease. The billets were then reweighed and the loading of silicone grease was determined by difference, as follows;

| Sample | Loading | Spectrum |
| --- | --- | --- |
| A | 8.7 mg/ft$^2$ | Fig. 4A |
| B | 2.8 mg/ft$^2$ | Fig. 4B |

An accessory built according to the invention was used to examine the surfaces of the two samples. The accessory comprised a framework, positionable mirror supports, and xyz-positionable attachment means made of aluminum. Two off-axis parabolic mirrors made from gold-plated nickel were placed in the mirror supports. A steel-sheathed optical fiber cable, comprising nineteen optical fibers made from chalcogenide glass that transmits in the mid-infrared range (approx. 900–5000 cm$^{-1}$) was attached by one end to the first xyz positioner. The other end of the cable was attached to the external beam port of a Bruker Vector 22 mid-infrared spectrometer. A second, similar optical fiber cable was attached to the second xyz positioner, and its other end was attached to a MCT detector unit which was cooled with liquid nitrogen and electrically coupled to the spectrometer. Before attempting to obtain spectra from the surfaces, the position of the first optical fiber cable was adjusted using the xyz positioning capability of the attachment means, so as to ensure that the end of the optical fiber bundle was at the focus of the first mirror, so that the beam from the cable would be collimated and reflected from the mirror onto the sample surface. Similarly, the position of the second cable end was adjusted to ensure that the end of the fiber optic bundle was at the focus of the second mirror, so that radiation reflected from the mirror would be focused onto the end of the fiber optic bundle. Both of the positionable attachment means were then tightened to prevent further movement.

Figure 6:
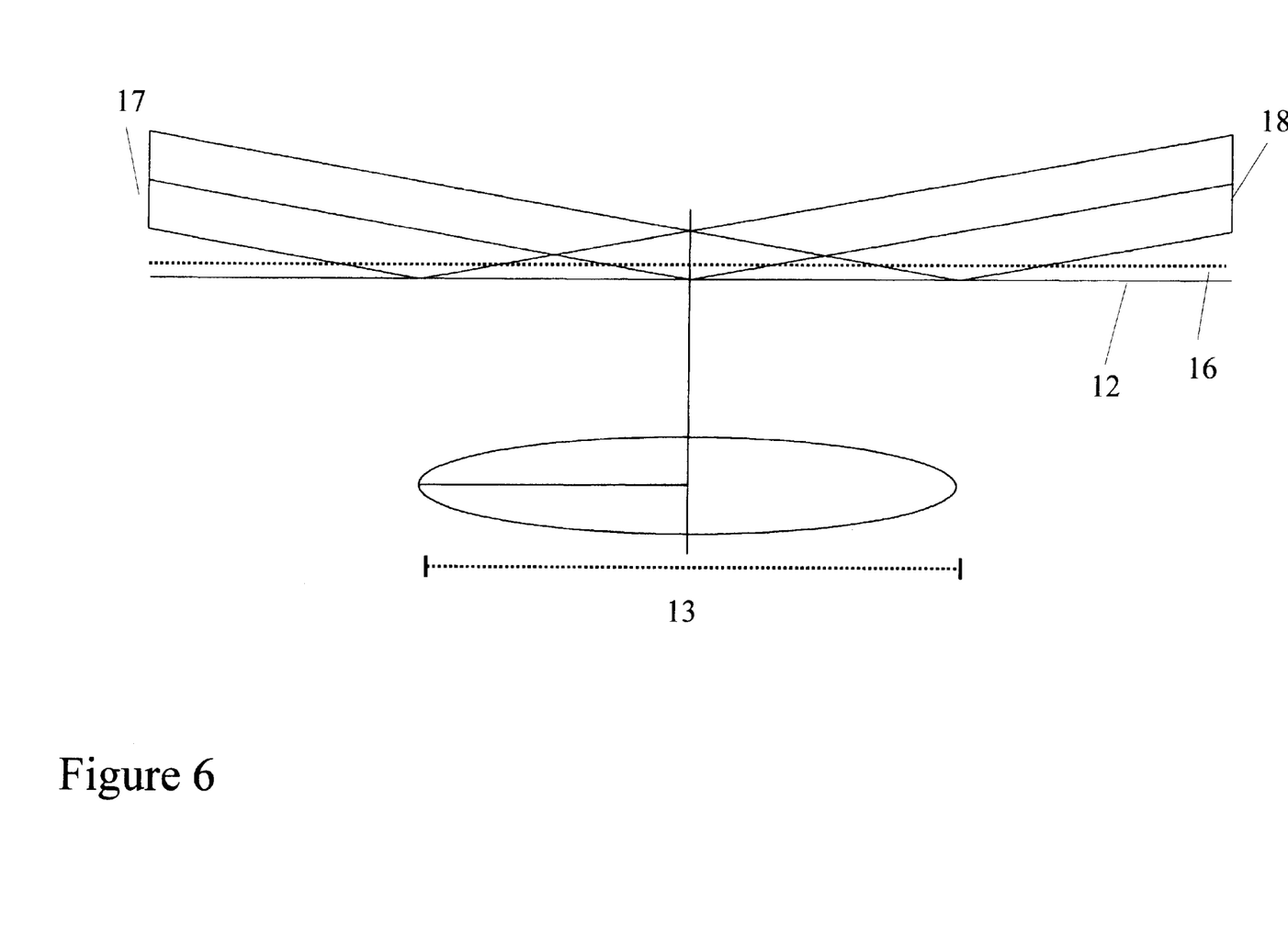
FIG. 6: Ray trace of the FTIR beam path at the grazing angle

The accessory was then placed on the surface of an ultraclean aluminum billet, and the positionable mirror supports were adjusted to provide the maximum path for the radiation passing through any film that might be present on the surface of a contaminated or coated sample. It will be understood by reference to FIG. 6, which is a ray trace of the radiation beam as it travels from mirror 4, by reflection from the surface, to mirror 5, that this is equivalent to maximizing the size of the spot formed by the radiation on the surface. This adjustment is best carried out by optimizing the signal level observed at the detector. After the adjustments were complete, a reference or background spectrum was obtained from the ultraclean sample. The accessory was then placed on the surfaces of samples A and B, and spectra were obtained.

The resulting mid-infrared spectra obtained from the samples A and B are shown in FIGS. 4A and 4B, respectively. Strong, sharp spectra characteristic of silicone grease are obtained in both cases.

Comparative Example 1

Sample B, with a loading of 2.8 mg/ft$^2$ silicone grease, was examined by direct specular reflectance, using a Remspec mid-IR fiber-optic probe attached to a Bruker Vector 22 spectrometer and an MCT detector. A reflectance probe as described in U.S. Pat. No. 5,754,722 was used. It was impossible to obtain a spectrum from the sample.

EXAMPLE 2

Figure 5:
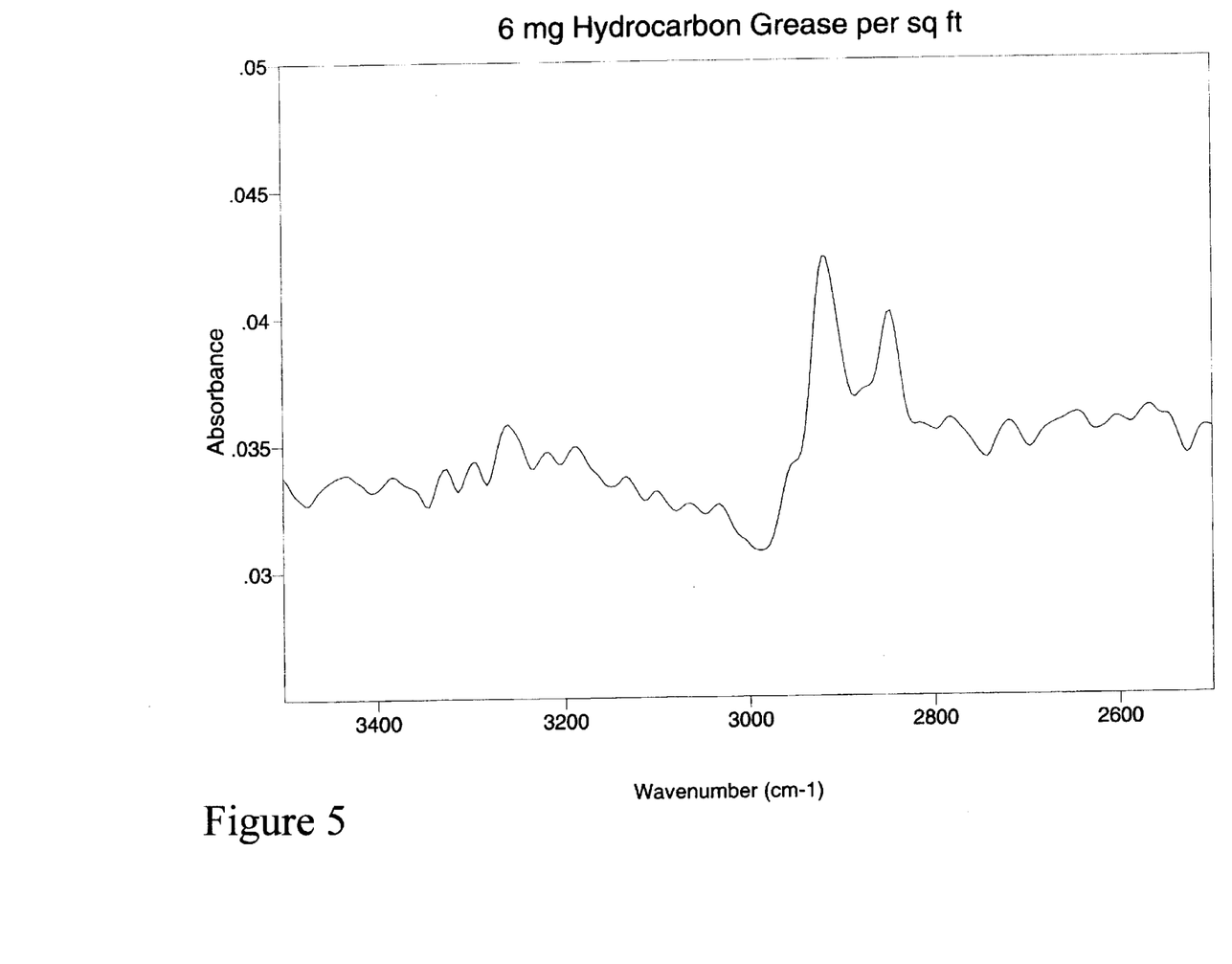
FIG. 5: Grazing-angle FTIR spectrum of hydrocarbon film on aluminum billet

An aluminum billet similar to those of Example 1 was air-brushed with hydrocarbon grease at a loading of 6 mg/ft$^2$. The equipment and the method of Example 1 were used to obtain the spectrum shown in FIG. 5.

What is claimed is:

1. A fiber-optic probe for use with a spectroscopic light source and a radiation detector, comprising a rigid framework having a base suitable to be placed directly onto a sample surface and characterized in that:

(a) the rigid framework is substantially open across the base part which is in contact with the sample surface (b) a first collimating mirror and a second focussing mirror are held within the rigid framework (c) a first fiber optic cable is attached at its first end to the spectroscopic light source and at its second end to the rigid framework such that radiation from the spectroscopic light source is directed through the first fiber optic cable onto the surface of the first collimating mirror from which it is reflected onto the sample surface (d) a second fiber optic cable is attached at its first end to the rigid framework and at its second end to the radiation detector such that the light reflected from the first collimating mirror onto the sample surface is subsequently reflected onto the second focussing mirror, from which it is reflected onto the end of the second fiber optic cable such that the reflected radiation is transmitted through the second fiber optic cable to the radiation detector.

2. The fiber-optic probe of claim 1, characterized in that the said first collimating mirror and the said second focussing mirror are held within the rigid framework by means of positionable holders such that they can be moved in relation to one another.

3. The fiber-optic probe of claim 1, characterized in that the spectroscopic light source is an infrared spectrometer, and the fiber-optic cables and the detector are operative in the infrared region of the spectrum.

4. The fiber-optic probe of claim 1, characterized in that the sample surface is a metal surface having a coating disposed upon it, wherein the coating comprises a material selected from the set comprising organic polymers, inorganic polymers, glasses, optically transparent inorganic oxides, organic oils, inorganic oils, organic lubricants, and inorganic lubricants.

5. The fiber-optic probe of claim 1, characterized in that the sample surface is a metal surface having a contamination disposed upon it, wherein the contamination comprises an organic compound.

6. The fiber optic probe of claim 1, characterized in that the sample surface is a metal surface having a contamination disposed upon it, wherein the contamination comprises a material selected from the set comprising a biologically active compound or an intermediate in the manufacture of a biologically active compound.

7. A fiber-optic probe for use with a spectroscopic light source and a radiation detector, comprising a rigid framework having a base suitable to be placed directly onto a sample surface and characterized in that:

(a) the rigid framework is substantially open across the base part which is in contact with the sample surface (b) a first collimating mirror and a second focussing mirror are held within the rigid framework by means of positionable holders such that they can be moved in relation to one another (c) a fiber optic cable is attached at its first end to the spectroscopic light source and at its second end to the rigid framework such that radiation from the spectroscopic light source is directed through the first fiber optic cable onto the surface of the first collimating mirror from which it is reflected onto the sample surface (d) the radiation detector is attached to the rigid framework such that the light reflected from the first collimating mirror onto the sample surface is subsequently reflected onto the second focussing mirror, from which it is reflected onto the radiation detector.

8. The fiber-optic probe of claim 7, characterized in that the said first collimating mirror and the said second focussing mirror are held within the rigid framework by means of positionable holders such that they can be moved in relation to one another.

9. The fiber-optic probe of claim 7, characterized in that the spectroscopic light source is an infrared spectrometer, and the fiber-optic cables and the detector are operative in the infrared region of the spectrum.

10. The fiber-optic probe of claim 7, characterized in that the sample surface is a metal surface having a coating disposed upon it, wherein the coating comprises a material selected from the set comprising organic polymers, inorganic polymers, glasses, optically transparent inorganic oxides, organic oils, inorganic oils, organic lubricants, and inorganic lubricants.

11. The fiber-optic probe of claim 7, characterized in that the sample surface is a metal surface having a contamination disposed upon it, wherein the contamination comprises an organic compound.

12. The fiber optic probe of claim 1, charecterized in that the sample surface is a metal surface having a contamination disposed upon it, wherein the contamination comprises a material selected from the set comprising a biologically active compound or an intermediate in the manufacture of a biologically active compound.

* * * * *